United States Patent
Foley et al.

(10) Patent No.: US 8,556,793 B2
(45) Date of Patent: Oct. 15, 2013

(54) CONTROL OF INTERFACE BETWEEN SEPARATED BLOOD COMPONENTS UNDER LIPEMIC AND HEMOLYTIC CONDITIONS

(75) Inventors: John T. Foley, Wheeling, IL (US); Lan T. Nguyen, Vernon Hills, IL (US); Jonathan Prendergast, Palatine, IL (US); Jeffrey Maher, Schaumburg, IL (US); Christopher Mikkelson, Round Lake Beach, IL (US)

(73) Assignee: Fenwal, Inc., Lake Zurich, IL (US)

( * ) Notice: Subject to any disclaimer, the term of this patent is extended or adjusted under 35 U.S.C. 154(b) by 365 days.

(21) Appl. No.: 13/021,346

(22) Filed: Feb. 4, 2011

(65) Prior Publication Data

US 2012/0199539 A1    Aug. 9, 2012

(51) Int. Cl.
*B01D 21/26*    (2006.01)

(52) U.S. Cl.
USPC .................................. 494/37; 494/10; 494/45

(58) Field of Classification Search
USPC .......... 494/10, 37, 43, 45; 210/745, 767, 782, 210/787; 604/4.01–6.16
See application file for complete search history.

(56) References Cited

U.S. PATENT DOCUMENTS

| | | | |
|---|---|---|---|
| 5,316,667 A | 5/1994 | Brown et al. | |
| 5,632,893 A | 5/1997 | Brown et al. | |
| 5,868,696 A | 2/1999 | Giesler et al. | |
| 6,254,784 B1 | 7/2001 | Nayak et al. | |
| 6,312,607 B1 | 11/2001 | Brown et al. | |
| 2004/0223857 A1 | 11/2004 | Kline et al. | |
| 2005/0051466 A1* | 3/2005 | Carter et al. | 494/10 |
| 2009/0129976 A1 | 5/2009 | Hoshino et al. | |

FOREIGN PATENT DOCUMENTS

EP    1 640 027 A1    3/2006

OTHER PUBLICATIONS

Search Report for European Patent Application No. 12153102.4, dated May 30, 2012.

* cited by examiner

*Primary Examiner* — Walter D Griffin
*Assistant Examiner* — Timothy Cleveland
(74) *Attorney, Agent, or Firm* — Cook Alex Ltd.

(57) ABSTRACT

Blood separation systems and methods are provided for controlling the interface between separated blood components. The system includes a blood separation chamber configured to separate blood into first and second blood components and an outlet line for removing at least a portion of the first blood component from the blood separation chamber. A primary optical sensor assembly is associated with the blood separation chamber to directly monitor the interior of the blood separation chamber. A secondary optical sensor assembly is associated with the outlet line to monitor the first blood component in the outlet line. The system also includes a controller programmed to select between the primary optical sensor assembly and the secondary optical sensor assembly for monitoring contamination of the first blood component. The system is particularly advantageous for preventing contamination of separated plasma which is lipemic or hemolytic.

5 Claims, 8 Drawing Sheets

CONTROL OF INTERFACE BETWEEN SEPARATED BLOOD COMPONENTS UNDER LIPEMIC AND HEMOLYTIC CONDITIONS

BACKGROUND

1. Field of the Disclosure

The invention relates to blood separation systems and methods. More particularly, the invention relates to systems and methods for preventing contamination of a separated blood component during processing.

2. Description of Related Art

Various blood processing systems now make it possible to collect particular blood constituents, rather than whole blood, from donors. Typically, in such systems, whole blood is drawn from a donor, the particular blood component or constituent is removed and collected, and the remaining blood constituents are returned to the donor. By thus removing only particular constituents, potentially less time is needed for the donor's body to return to normal, and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the donor. To avoid contamination and possible infection of the donor, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber in the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of a separation chamber included as part of the fluid processing assembly. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid processing assembly. For example, therapeutic plasma exchange involves separating plasma from cellular blood components, collecting the plasma, and returning the cellular blood components and a replacement fluid to the donor.

Proper separation requires, however, that the interface between the separated components be located within a particular zone between the high-G and low-G walls of the separation chamber. For example, when performing a therapeutic plasma exchange procedure, the interface between the plasma and the cellular blood components affects the performance of the system. If the interface is located too close to the low-G wall, then the collected plasma may become unduly populated or contaminated by cellular blood components. On the other hand, if the interface is located too far from the low-G wall, there may be no contamination of the plasma, but the separation efficiency of the system may be decreased with less plasma collected over time.

Various known centrifuges, such as those shown and described in U.S. Pat. Nos. 6,254,784 to Nayak et al. and 6,312,607 to Brown et al. (which are incorporated herein by reference), are operable to automatically keep the interface within a desired zone as the centrifuge operates. Typically, the separation chamber of the fluid processing assembly is loaded between the bowl and spool of a centrifuge. A radially inwardly ramped surface is located on the radially outer wall of the separation channel in the bowl wall of the separation chamber. The interface between the generally dark, opaque red blood cell layer and the generally light, clear plasma layer appears as a line on the ramped surface. Where, exactly, the line appears on the ramped surface is a function of the position of the interface between the high-G and low-G walls of the separation chamber. Accordingly, the position of the line on the ramped surface can be used to gauge the position of the interface between the high-G and low-G walls.

Automatic control over the location of the interface has been achieved by sensing the position of the line on the ramped surface and thereafter adjusting the centrifuge operating parameters to place and keep the line within desired limits. In particular, by controlling the rate at which plasma is withdrawn from the separation chamber, the line can be "moved" up (radially inwardly) or down (radially outwardly) on the ramped surface, such as by decreasing or increasing the plasma flow rate. Typically, an optical sensor assembly is used to sense the position of the line on the ramped surface. As the centrifuge spins past the sensor, the sensor develops an electrical pulse having a width related to the position of the line on the ramped surface. As the line moves closer to the high g wall of the separation chamber, the pulse width increases. As the line moves closer to the low-G wall, the pulse width narrows. By sensing the width of the pulses developed by the optical sensor and thereafter using the pulse width to increase or decrease the rate at which plasma is withdrawn from the separation chamber, the line can be kept within desired positional limits on the ramped surface and the interface maintained in the desired radial position or range of positions.

However, experience has shown that a variety of abnormalities or unusual operating conditions may arise that make pulse width, by itself, a less reliable indicator of proper interface positioning. For example, lipemia (unusually high lipid concentration) or hemolysis (unusually high amounts of free hemoglobin due to ruptured red blood cells) in the donor's blood can change the percentage of light transmitted through the plasma and thus the apparent width of the detected pulses with no real change in the actual position of the interface line on the ramped surface. Accordingly, the need remains for a centrifugal blood processing system which can provide more accurate readings of the actual location of the interface, when conditions impair accuracy.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood separation system is provided with a blood separation chamber configured to separate at least one blood component from blood. An outlet line is associated with the blood separation chamber for removing at least a portion of the one blood component from the blood separation chamber. A first optical sensor assembly is configured to directly monitor the interior of the blood separation chamber and a second optical sensor assembly is configured to monitor the contents of the outlet line and produce an output. The system also includes a controller configured to select, during a blood separation procedure, the first optical sensor assembly or the second optical sensor assembly for process monitoring based at least in part on the output of the second optical sensor assembly.

In another aspect, a method is provided for separating blood into one blood component and other blood components. The method includes separating at least one blood component from blood in a blood separation chamber and monitoring the interior of the blood separation chamber with a first optical sensor assembly. At least a portion of the one blood component is removed from the blood separation chamber and monitored with a second optical sensor assembly. While blood is being separated, the first optical sensor assembly or the secondary optical sensor assembly is selected for process monitoring.

In yet another aspect, a blood separation system is provided with a blood separation chamber configured to separate blood into plasma and cellular blood components. An outlet line is associated with the blood separation chamber for removing at least a portion of the plasma from the blood separation chamber. A pump is associated with the outlet line for conveying plasma through the outlet line. A first optical sensor assembly is configured to directly monitor the interior of the blood separation chamber and a second optical sensor assembly is configured to monitor the plasma in the outlet line. A controller is configured to control the operation of the pump and to select between the first optical sensor assembly and the second optical sensor assembly for detecting the presence of cellular blood components in the plasma. The controller selects between the first optical sensor assembly and the second optical sensor assembly during a blood separation procedure and the selection is based at least in part on an optical characteristic of the plasma.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
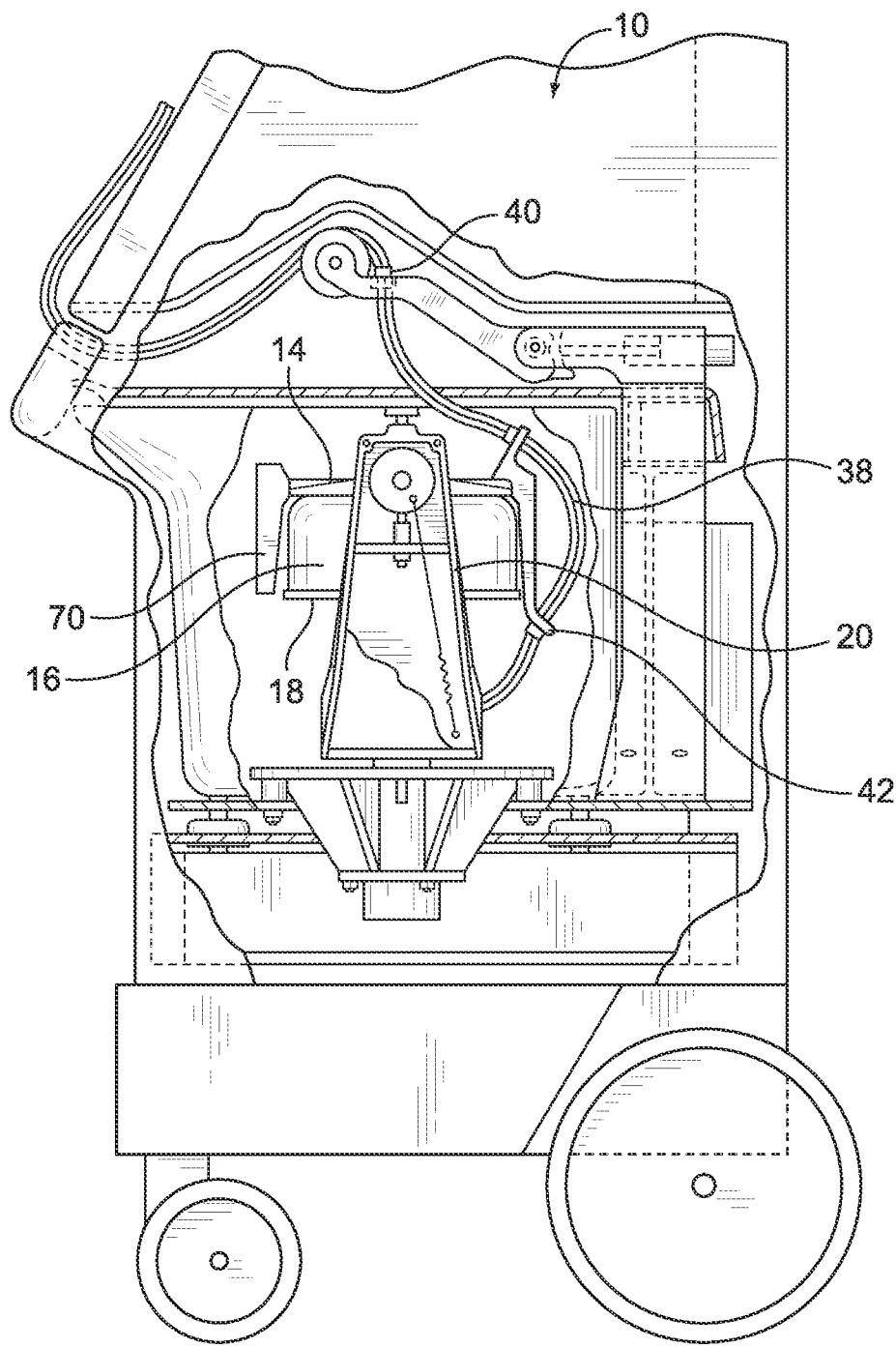
FIG. 1 is a side elevation view, with portions broken away and in section, of a blood separation system employing aspects of the present invention, with a centrifuge bowl and spool of the system being shown in their operating position.
Figure 2:
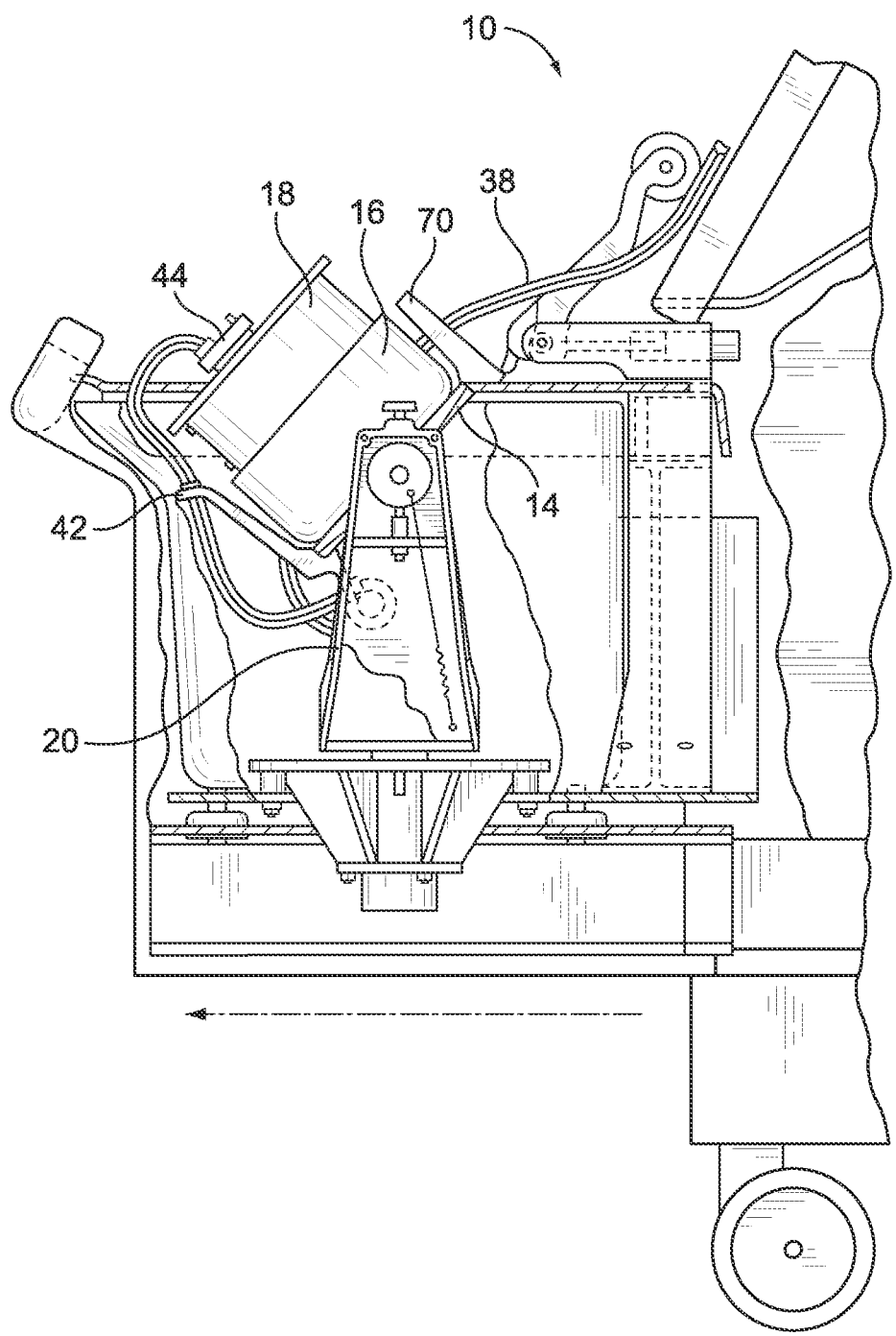
FIG. 2 is a side elevation view, with portions broken away and in section, of the system shown in FIG. 1, with the bowl and spool shown in an upright position for receiving a blood separation chamber.

FIGS. 1 and 2 show a centrifugal fluid processing system 10 with an interface controller 12 (FIG. 11) that may be used in practicing the interface control principles of the present disclosure. The system is currently marketed as the AMICUS® separator by Fenwal, Inc. of Lake Zurich, Ill., as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials. While interface control principles will be described herein with reference to one particular system 10, it should be understood that these principles may be employed with other fluid processing systems employing different interface control systems without departing from the scope of the present disclosure.

A. The Centrifuge

The system 10 includes a centrifuge 14 used to centrifugally separate blood components. The system 10 may be programmed to separate blood into a variety of components (e.g., platelet-rich plasma and red cells). For illustrative purposes, a therapeutic plasma exchange procedure, in which the centrifuge 14 separates whole blood into cellular components (e.g., red blood cells and platelets) and substantially cell-free plasma, will be described herein. However, the principles described and claimed herein may be employed with other blood separation procedures without departing from the scope of the present disclosure.

The illustrated centrifuge 14 is of the type shown in U.S. Pat. No. 5,316,667 to Brown et al., which is incorporated herein by reference. The centrifuge comprises a bowl 16 and a spool 18. The bowl 16 and spool 18 are pivoted on a yoke 20 between an operating position (FIG. 1) and a loading/unloading position (FIG. 2).

When in the loading/unloading position, the spool 18 can be opened by movement at least partially out of the bowl 16, as FIG. 2 shows. In this position, the operator wraps a flexible blood separation chamber 22 (see FIG. 3) about the spool 18. Closure of the spool 18 and bowl 16 encloses the chamber 22 for processing. When closed, the spool 18 and bowl 16 are pivoted into the operating position of FIG. 1 for rotation about an axis.

B. The Blood Separation Chamber

Figure 4:
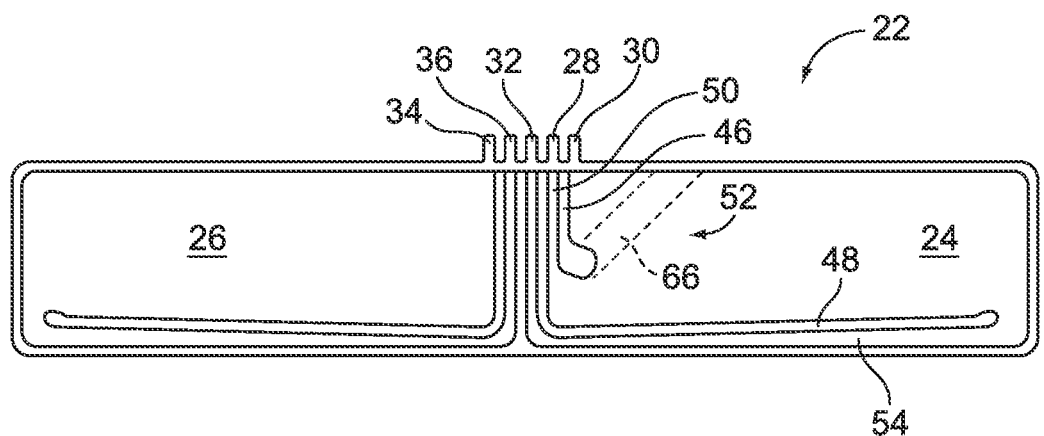
FIG. 4 is a plan view of the blood separation chamber shown in FIG. 3, out of association with the spool.

The blood separation chamber 22 can be variously constructed. FIG. 4 shows a representative embodiment.

The chamber 22 shown in FIG. 4 allows for either single- or multi-stage processing. When used for multi-stage processing, a first stage 24 separates whole blood into first and second components. Depending on the nature of the separation procedure, one of the components may be transferred into a second stage 26 for further processing.

Figure 3:
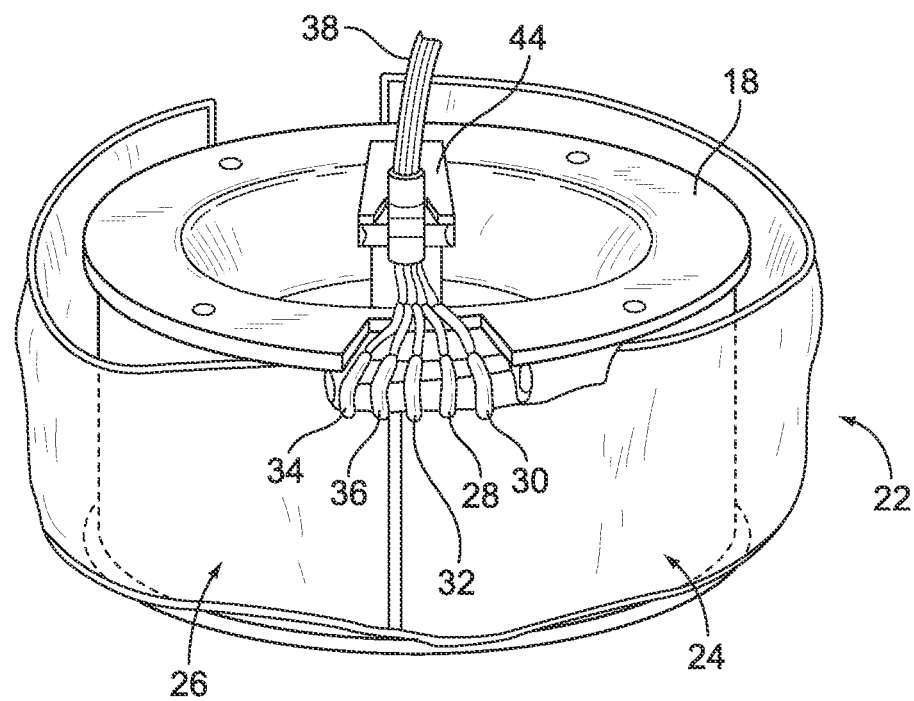
FIG. 3 is a top perspective view of the spool of the centrifuge shown in FIG. 2 in its upright position and carrying the blood separation chamber.

As FIGS. 3 and 4 best show, there are three ports 28, 30, and 32 associated with the first stage 24. Depending on the particular blood processing procedure, the ports may have different functionality but, in a therapeutic plasma exchange procedure, the port identified at 32 is used for conveying blood from a blood source or donor into the first stage 24. During such a therapeutic plasma exchange procedure, the other two ports 28 and 30 serve as outlet ports for separated blood components exiting the first stage 24. More particularly, the first outlet port 30 conveys a low density blood component from the first stage 24, while the second outlet port 28 conveys a high density blood component from the first stage 24.

In a method of carrying out single-stage processing, one of the separated components is returned to the donor, while the other is removed from the first stage 24 and stored. For example, when carrying out a therapeutic plasma exchange procedure, whole blood in the first stage 24 is separated into cellular components (i.e., a high density component) and substantially cell-free plasma (i.e., a low density component). The plasma is removed from the first stage 24 via the first outlet port 30 for collection and storage, while the cellular components are removed from the first stage 24 via the second outlet port 28 and returned to the donor or patient. Alternatively, rather than collecting and storing the plasma, it may instead be discarded after separation or treated by a secondary device (e.g., an adsorption column) and returned to the donor or patient.

If multi-stage processing is required, one of the components will be transferred from the first stage 24 to the second stage 26 via a port 34 associated with the second stage 26. The component transferred to the second stage 26 is further fractionated into sub-components, with one of the sub-components being removed from the second stage 26 via an outlet port 36 and the other sub-component remaining in the second stage 26. In the illustrated embodiment, the ports 28, 30, 32, 34, and 36 are arranged side-by-side along the top transverse edge of the chamber 22.

While the same ports 28, 30, and 32 of the first stage 24 are used as in the above-described therapeutic plasma exchange procedure, the ports 28 and 32 have different functionality in a multi-stage separation procedure. In one method of multi-stage operation, blood enters the first stage 24 via the port 28 and is separated into red blood cells (i.e., the high density blood component) and platelet-rich plasma (i.e., the low density blood component). The red blood cells are returned to the donor (via the port 32), while the platelet-rich plasma is conveyed out of the first stage 24 (via the first outlet port 30) and into the second stage 26 (via the inlet port 34). In the second stage 26, the platelet-rich plasma is separated into platelet-poor plasma and platelet concentrate. The platelet-poor plasma is removed from the second stage 26 (via the outlet port 36), leaving platelet concentrate in the second stage 26 for resuspension and transfer to one or more storage containers.

As best shown in FIG. 3, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 4 shows, a first interior seal 46 is located between the low density outlet port 30 and the high density outlet port 28. A second interior seal 48 is located between the high density outlet port 28 and the blood inlet port 32. The interior seals 46 and 48 form a fluid passage 50 (an outlet for high density blood components in a therapeutic plasma exchange procedure) and a low density collection region 52 in the first stage 24. The second seal 48 also forms a fluid passage 54 (a blood inlet in a therapeutic plasma exchange procedure) in the first stage 24.

Figure 5:
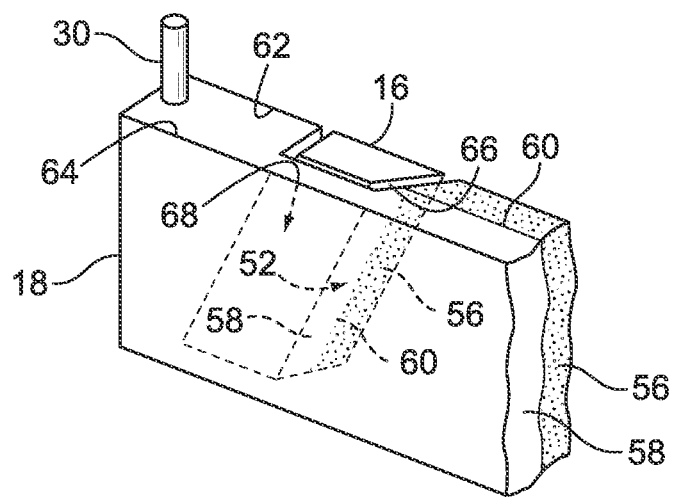
FIG. 5 is an enlarged perspective view of an interface ramp carried by the centrifuge in association with the blood separation chamber, showing the centrifugally separated red blood cell layer, plasma layer, and interface within the chamber when in a desired location on the ramp.

In a therapeutic plasma exchange procedure, the fluid passage 54 channels blood directly into the circumferential flow path immediately next to the low density collection region 52. As shown in FIG. 5, the blood separates into an optically dense layer 56 containing cellular components, which forms as cellular components move under the influence of centrifugal force toward the high-G (outer) wall 62. The optically dense layer 56 will include red blood cells (and, hence, will be referred to herein as the "RBC layer") but, depending on the speed at which the centrifuge 14 is spun, other cellular components (e.g., larger white blood cells and platelets) may also be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer") but, depending on the speed at which the centrifuge 14 is rotated and the length of time that the blood is resident in the centrifuge, other components (e.g., platelets and smaller white blood cells) may also be present in the plasma layer 58.

The transition between the formed cellular blood components and the liquid plasma component is generally referred to as the interface 60 (FIG. 5). Platelets and white blood cells (which have a density greater than plasma and usually less than red blood cells) typically occupy this transition region, although that also varies with centrifuge speed and residence time, as is well known in the technical field.

Figure 6:
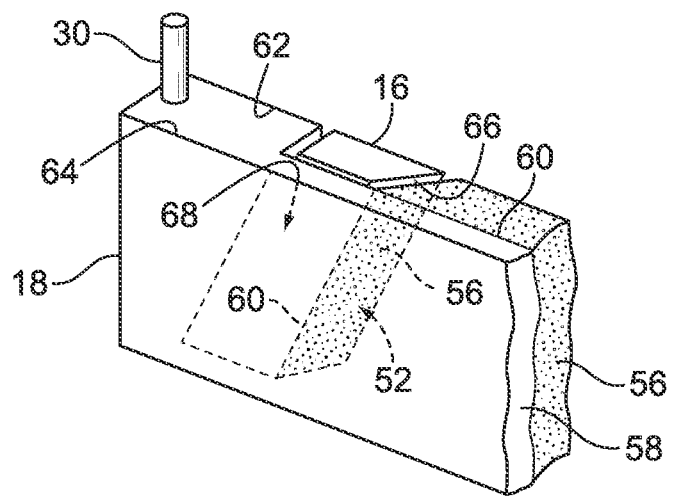
FIG. 6 is an enlarged perspective view of the interface ramp shown in FIG. 5, showing the red blood cell layer and interface at an undesired high location on the ramp.
Figure 7:
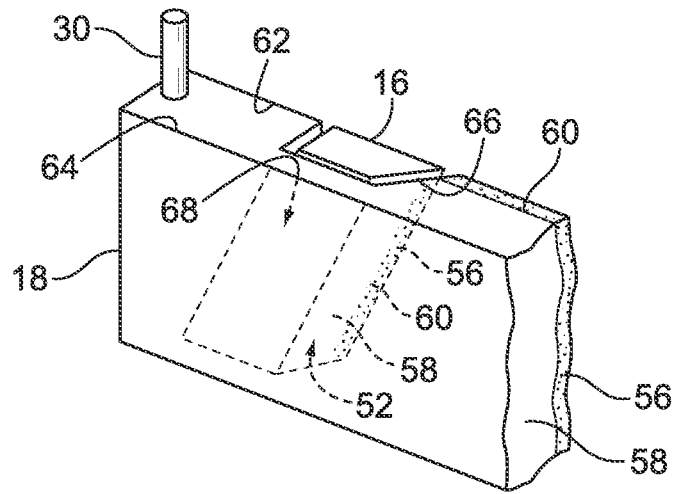
FIG. 7 is an enlarged perspective view of the interface ramp shown in FIG. 5, showing the red blood cell layer and interface at an undesired low location on the ramp.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), cellular components can spill over and into the low density collection region 52, adversely affecting the quality of the low density components (typically plasma). On the other hand, if the location of the interface 60 is too low (that is, if it resides too far away from the low-G wall 64, as FIG. 7 shows), the collection efficiency of the system 10 may be impaired.

As FIG. 5 shows, a ramp 66 extends from the high-G wall 62 of the bowl 16 at an angle across the low density collection region 52. The angle, measured with respect to the axis of the first outlet port 30 is about 30° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893 to Brown et al., which is incorporated herein by reference.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667, which is incorporated by reference.

C. The Interface Controller

The interface controller 12 (FIG. 11) includes a viewing head or first optical sensor assembly 70 carried on the yoke 20 (see FIGS. 1 and 8) and a second optical sensor assembly 72 which is associated with tubing connected to the first outlet port 30. The first optical sensor assembly 70 is oriented to optically view the transition in optical density between the RBC layer 56 and the plasma layer 58 on the ramp 66. The second optical sensor assembly 72 monitors the optical density of fluid exiting the first stage 24 via the first outlet port 30.

The interface controller 12 is functional to determine the location of the interface 60 on the ramp 66 and, if the interface 60 is located at an improper location (e.g., in the locations of FIG. 6 or 7), to correct the location of the interface 60.

(1) The First Optical Sensor Assembly

Figure 8:
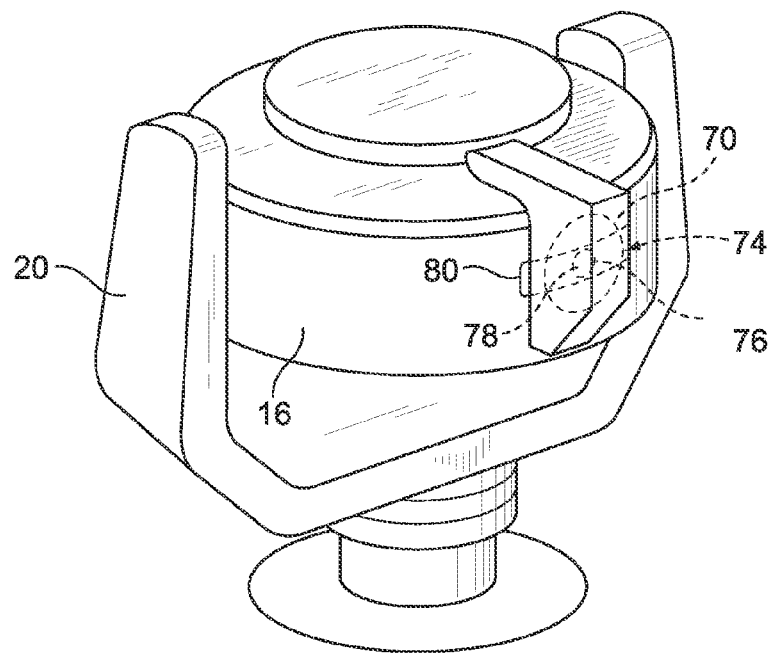
FIG. 8 is a side perspective view of the bowl and spool of the centrifuge when in the operating position, showing a viewing head, which forms a part of the interface controller, being carried by the centrifuge to view the interface ramp during rotation of the bowl.
Figure 9:
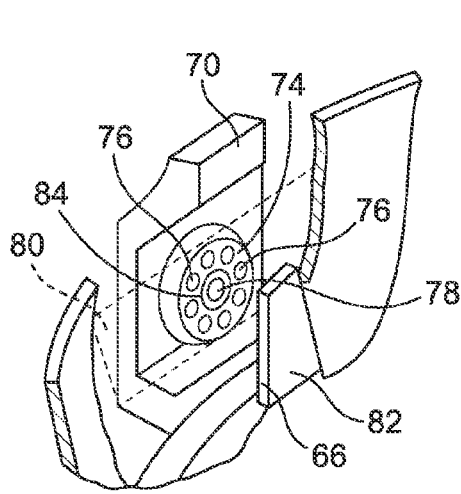
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
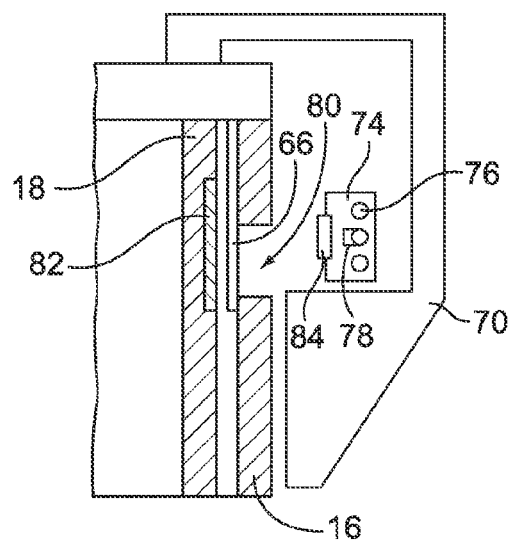
FIG. 10 is a side section view of the bowl, spool, and viewing head when the viewing head is aligned with the interface ramp.

Referring to FIGS. 8-10, the first optical sensor assembly 70, carried by the yoke 20, includes a light source 74, which emits light that is absorbed by red blood cells. In the illustrated embodiment, the light source 74 includes a circular array of red light emitting diodes 76, but other wavelengths absorbed by red blood cells, like green or infrared, could also be used.

In the illustrated embodiment, seven light emitting diodes 76 comprise the light source 74. More diodes 76 may be used, or fewer diodes 76 can be used, depending upon the optical characteristics desired. Further, non-LED lights may also be employed without departing from the scope of the present disclosure.

The first optical sensor assembly 70 also includes a light detector 78 (FIGS. 9 and 10), which is mounted adjacent to the light source 74. In one embodiment, the light detector 78 comprises a PIN diode detector, which is located generally in the geometric center of the circular array of light emitting diodes 76. Other types of light detectors may also be employed.

The yoke 20 and the first optical sensor assembly 70 rotate at a one omega speed, as the spool 18 and bowl 16 rotate at a two omega speed. The light source 74 directs light onto the rotating bowl 16. In the illustrated embodiment, the bowl 16 is transparent to the light emitted by the source 74 only in the region 80 where the bowl 16 overlies the interface ramp 66 (FIG. 8). In the illustrated embodiment, the region 80 comprises a window cut out in the bowl 16. The remainder of the bowl 16 that lies in the path of the first optical sensor assembly 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and first optical sensor assembly 70 align. The spool 18 may also carry a light reflective material 82 (FIGS. 9 and 10) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 9 and 10), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the first optical sensor assembly 70, the detector 78 will first sense light reflected through the plasma layer 58 on the ramp 66. Eventually, the RBC layer 56 adjacent the interface 60 on the ramp 66 will enter the optical path of the first optical sensor assembly 70. The RBC layer 56 absorbs light from the source 74 and thereby reduces the previously sensed intensity of the reflected light. The intensity of the reflected light sensed by the detector 78 represents the amount of light from the source 74 that is not absorbed by the RBC layer 56 adjacent to the interface 60. With this information, a processing element or module 86 (FIG. 11) can determine the location of the interface 60 on the ramp 66 relative to the constricted passage 68. A more detailed discussion of the algorithms by which the interface controller 12 receives and processes signals to determine the location of the interface 60 on the ramp 66 may be found in U.S. Pat. No. 6,312,607 to Brown et al., which is incorporated herein by reference.

Figure 11:
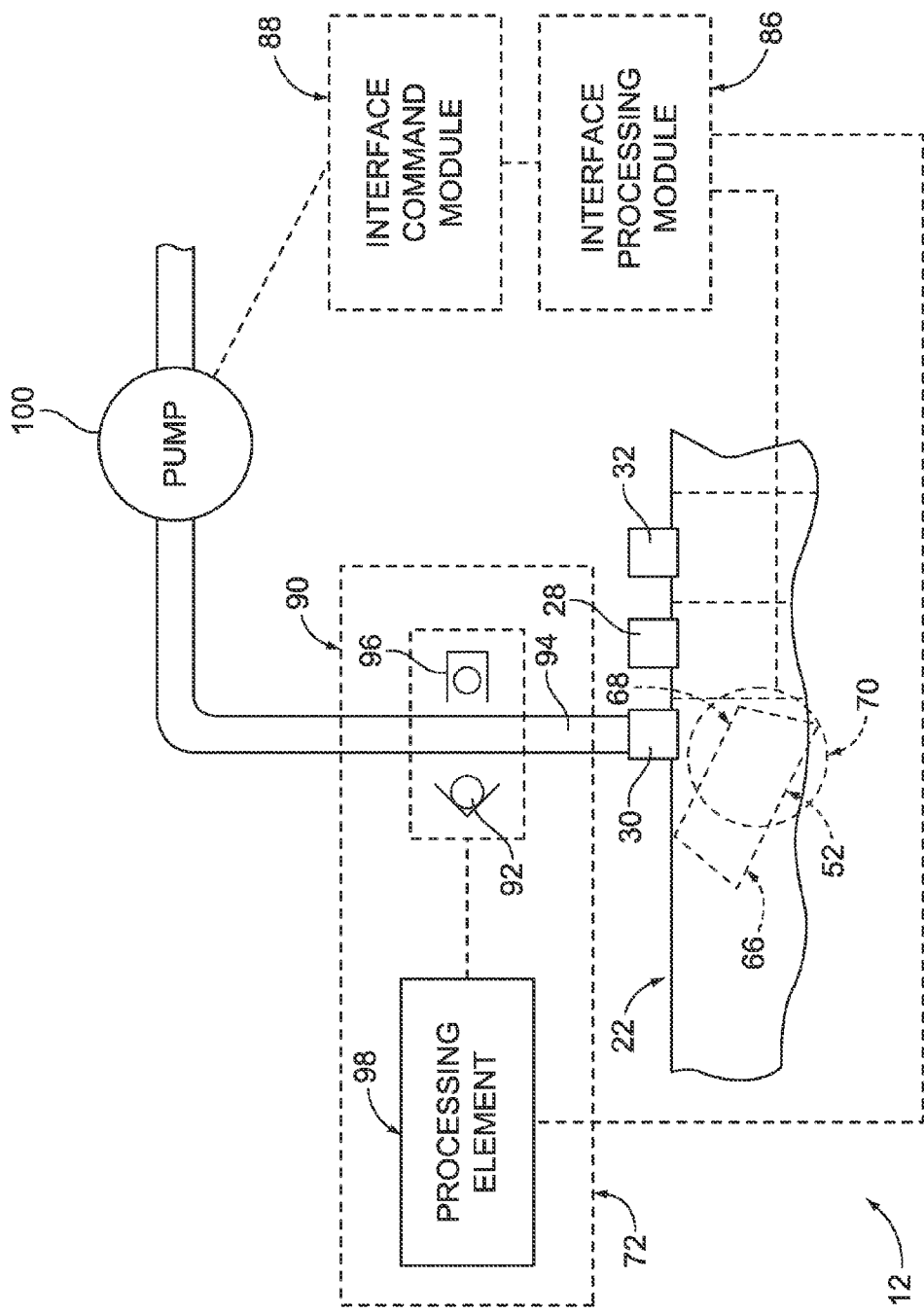
FIG. 11 is a schematic view of a blood calibration element, which forms a part of the interface controller.

When the location of the interface 60 on the ramp 66 has been determined, the processing element 86 outputs that information to an interface command element or module 88 (FIG. 11). The command element 88 includes a comparator, which compares the interface location output with a desired interface location to generate an error signal. The error signal may take a number of forms but, in one embodiment, is expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too large (as FIG. 6 shows). The interface command element 88 generates a signal to adjust an operational parameter accordingly, such as by reducing the rate at which plasma is removed through the first outlet port 30 under action of a pump 100 (FIG. 11). The interface 60 moves away from the constricted passage 68 toward the desired control position (as FIG. 5 shows), where the error signal is zero.

A negative error signal indicates that the RBC layer 56 on the ramp 66 is too small (as FIG. 7 shows). The interface command element 88 generates a signal to adjust an operational parameter accordingly, such as by increasing the rate at which plasma is removed through the first outlet port 30. The interface 60 moves toward the constricted passage 68 to the desired control position (FIG. 5), where the error signal is again zero.

(2) The Second Optical Sensor Assembly

The interface controller 12 further includes a second optical sensor assembly 72 (FIG. 11), which is configured to monitor the optical density of plasma outside of the blood separation chamber 22. The second optical sensor assembly 72 may be positioned anywhere in the fluid circuit outside of the blood separation chamber 22 where separated plasma is present but, in the illustrated embodiment is associated with tubing 94 connected to the first outlet port 30 so as to monitor plasma exiting the first stage 24. The second optical sensor assembly 72 compares the optical density of separated plasma to a baseline fluid (e.g., saline) exiting the first outlet port 30. If the optical density of the plasma is significantly different from saline, then it may be indicative of lipemic or hemolytic conditions, as will be described in greater detail herein.

The second optical sensor assembly 72 includes an optical monitor 90 (see FIG. 11), which senses the optical density of fluid exiting the first outlet port 30 or (in the case of a multi-stage separation procedure) entering the second stage inlet port 34. In one embodiment, the optical monitor 90 is a conventional hemoglobin detector of the type used on the Autopheresis-C® blood processing device sold by Fenwal, Inc. of Lake Zurich, Ill. The optical monitor 90 comprises a red light-emitting diode 92, which emits light into the outlet tubing 94 connected to the first outlet port 30 on the outside of the blood separation chamber 22. The optical monitor 90 further includes a PIN diode detector 96 on the opposite side of the tubing 94.

Different or additional light sources could also be used without departing from the scope of the present disclosure. For example, it may be advantageous to include separate red and green light-emitting diodes to distinguish between lipemic and hemolytic conditions in the whole blood and/or plasma layer 58. If, when considering plasma in the tubing 94, the overall transmissivity of the plasma is below a certain level (indicating that the plasma is relatively turbid and may be either lipemic or hemolytic), the red and green transmissions are separately considered. If the red and green transmissions decrease by a similar percentage (from the level of transmission through saline), then it is indicative of lipemia (because green and red light are absorbed to a similar extent by lipids). However, if the green transmission decreases to a much greater degree than the red transmission, it is indicative of hemolytic plasma (because green light is more readily absorbed by hemoglobin than red light).

The second optical sensor assembly 72 also includes a processing element 98, which receives signals from the monitor 90 to compute the optical transmission of the liquid conveyed through the tubing 94. A more detailed discussion of a set of exemplary algorithms by which the optical densities of the tubing 94 itself, saline present in the tubing 94, and plasma in the outlet tubing 94 may determined can be found in U.S. Pat. No. 6,312,607.

D. Dual-Sensor Pump and Contamination Detection Control

The optical density of the plasma layer 58 will vary according to the concentration of lipids and/or hemoglobin in the plasma, which depends upon the physiology or morphology of the individual donor. Lipemic or hemolytic plasma has an optical density that differs significantly from saline or non-lipemic/hemolytic plasma. As a result, the presence of plasma on the ramp 66 carrying high concentrations of lipids (lipemia) or hemoglobin (hemolysis) diminishes the magnitude of the sensed voltage signals, independent of and unrelated to changes in the physical dimensions of the interface. Accordingly, the first optical sensor assembly 70 may, in that situation, have reduced accuracy in monitoring the location of the interface 60 and any occurrence of plasma contamination.

As shown in FIG. 11, the processing element 98 of the second optical sensor assembly 72 is associated with the interface processing element or module 86, which is, in turn, associated with the interface command element or module 88. Accordingly, data collected and processed by the processing element 98 of the second optical sensor assembly 72 may be considered when determining the location of the interface 60 and/or taking corrective action to reposition the interface 60. In particular, the data collected by the second optical sensor assembly 72 may be employed for interface or contamination detection control as outlined in FIG. 12.

Figure 12A:
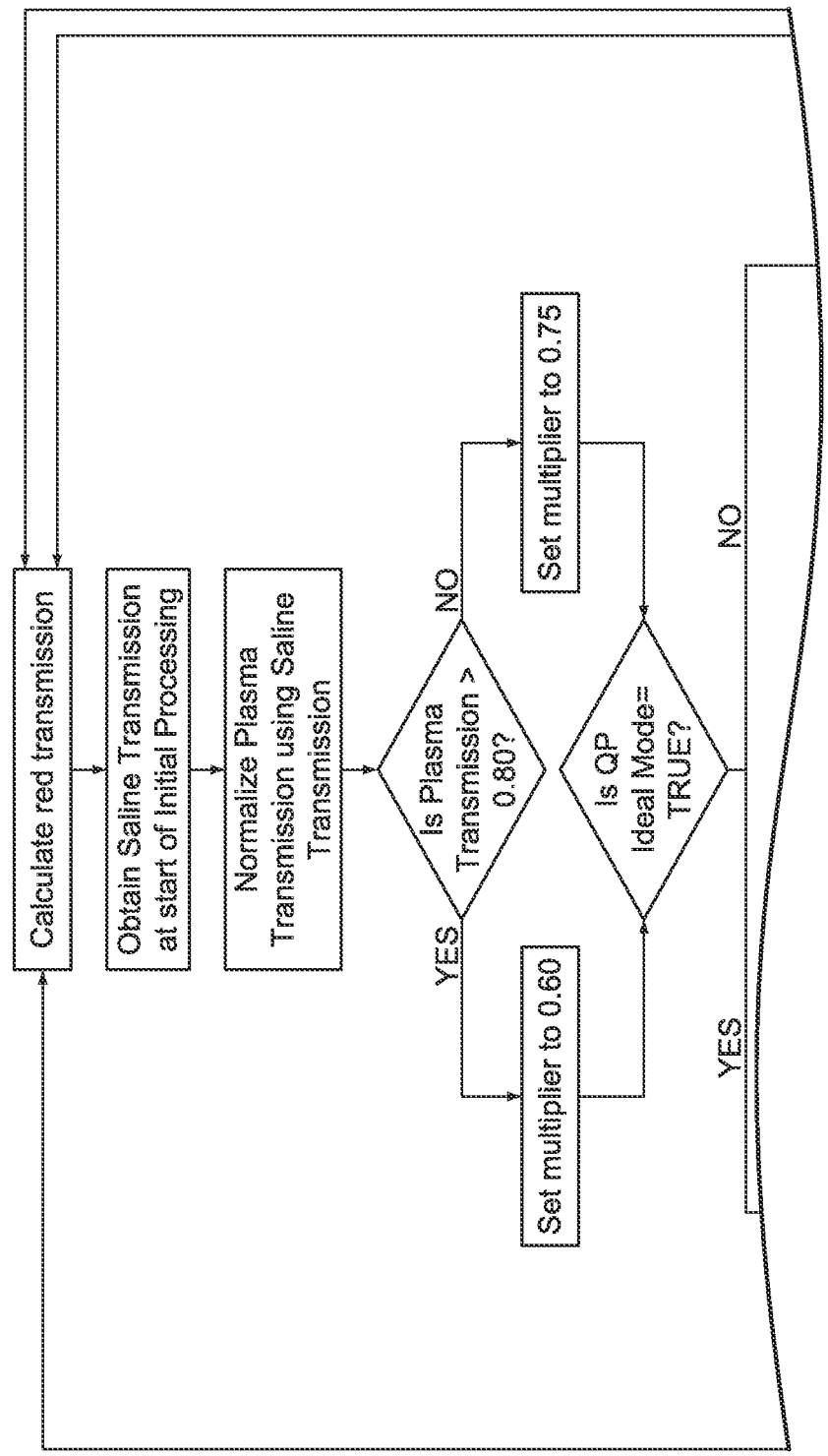
FIGS. 12A and 12B are first and second portions of a flowchart which shows the process undertaken by the interface controller when selecting the interface control mode.
Figure 12B:
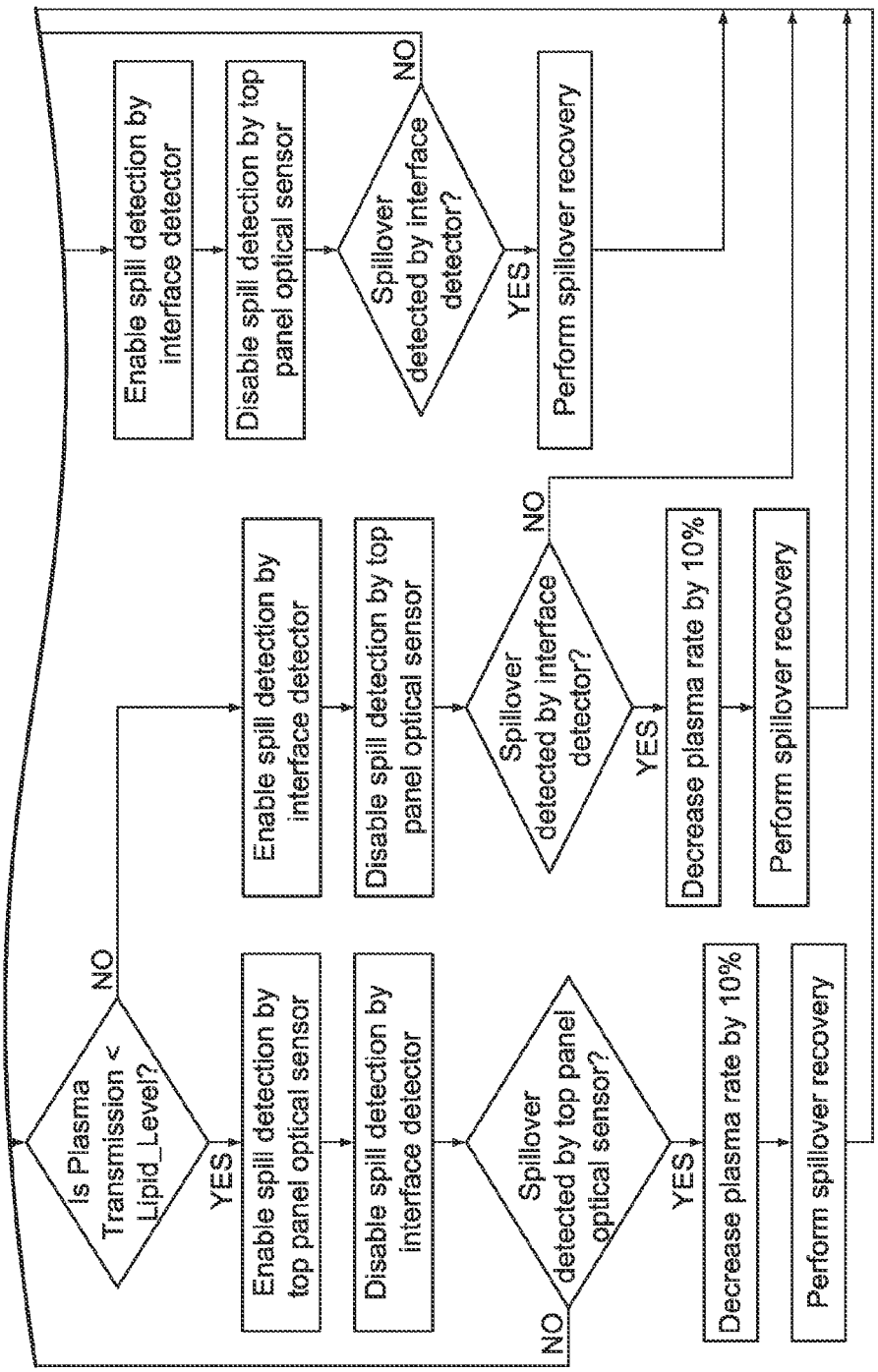

The control scheme outlined in FIGS. 12A and 12B includes two parts, a pump control module (illustrated generally in FIG. 12A) and a contamination detection module (illustrated generally in FIG. 12B), which may be employed together or individually. It may be preferred to employ the modules together, as the pump control module helps to improve the collection efficiency of the system, while the contamination detection module selects the most appropriate sensor assembly for monitoring separated plasma and preventing contamination thereof.

The control scheme outlined in FIGS. 12A and 12B will be described herein with reference to a second optical sensor assembly 72 having only a red light-emitting diode as a light source 92. Such a simplified second optical sensor assembly 72 can be used to identify plasma turbidity, but may not distinguish between lipemic and hemolytic conditions. In one embodiment, the same diagnostic and corrective steps are taken regardless of whether lipemic or hemolytic conditions are present, so it is unnecessary to determine whether turbid plasma is lipemic vs. hemolytic. However, a more advanced interface controller 12 (e.g., one with a second optical sensor assembly 72 capable of distinguishing between lipemic and hemolytic conditions) may also be employed without departing from the scope of the present disclosure. A more advanced interface controller 12 may be advantageous when employing a control scheme which takes different diagnostic and/or corrective steps depending on whether turbid plasma is lipemic or hemolytic.

First, prior to fluid processing, the effect of the outlet tubing 94 on the transmission of light therethrough may be determined by the processing element 98 of the second optical sensor assembly 72. This may be achieved in any of a number of ways but, in one embodiment, involves taking a variety of measurements of the light which passes through and the light which does not pass through the empty outlet tubing 94. For example, these measurements may include: (1) the amount of light from the light source 92 which passes through the outlet tubing 94, (2) the amount of light from the light source 92 which does not pass through the outlet tubing 94, (3) the amount of background light which passes through the outlet tubing 94, and (4) the amount of background light which does not pass through the outlet tubing 94. Typically, measurements of the background light are taken while the light source 92 is turned off.

The amount of light from the light source 92 which passes through the outlet tubing 94 is subtracted from the amount of background light which passes through the outlet tubing 94 to arrive at a "corrected transmitted light" value. Similarly, the amount of light from the light source 92 which does not pass through the outlet tubing 94 is subtracted from the amount of background light which does not pass through the outlet tubing 94 to arrive at a "corrected non-transmitted light" value. The "corrected transmitted light" value may be divided by the "corrected non-transmitted light" value to arrive at a normalized value which accounts for the effect of the outlet tubing 94 on the transmission of light therethrough. This "correction factor" may be used to correct any future measurements taken during fluid processing.

With the "correction factor" so calculated, saline is then pumped into and through the system to prime the system. As the saline exits the first stage 24 via the first outlet port 30, the transmission of light from the light source 92 (red light in one embodiment) through the outlet tubing 94 is measured by the processing element 98. The "correction factor" may be applied to the measured value to arrive at a corrected or normalized measurement of the red light transmitted through the tubing 94 and saline. This process is represented in FIG. 12A by the box containing the words "Obtain Saline Transmission at start of Initial Processing."

When the system has been suitably primed, blood from a blood source is pumped into the first stage 24, where it is separated into a plasma layer 58 and an RBC layer 56, with an interface 60 therebetween. The plasma layer 58 is removed from the first stage 24 via the first outlet port 30 (under action of the pump 100), while the RBC layer 56 exits the first stage 24 via the second outlet port 28.

The second optical sensor assembly 72 monitors fluid flowing from the first outlet port 30, and periodically assesses the transmissivity of the plasma layer 58 in the tubing 94. As when determining the transmissivity of saline moving through the tubing 94, the processing element 98 of the second optical sensor assembly 72 may apply the "correction factor" to the measured value to arrive at a corrected or normalized measurement of the red light transmitted through the tubing 94 and plasma.

When the second optical sensor assembly 72 has determined both the transmissivity of light through the saline-filled tubing 94 and the transmissivity of light through the plasma-filled tubing 94, the plasma transmission is normalized by dividing the plasma transmissivity by the saline transmissivity. The higher the normalized transmission value is (up to a maximum value of 1.0, which indicates a plasma layer 58 as clear as saline), the clearer the plasma layer 58. The normalized transmission value is employed as an input or control factor for both the pump control module and the contamination detection module of the control scheme. This process is represented in FIG. 12A by the box containing the words "Normalize Plasma Transmission using Saline Transmission."

(1) Pump Control Module

The pump control module helps to improve the collection efficiency of the system by selecting the speed at which at least one of the pumps of the system operates based on the light transmissivity of a separated blood component. A specific implementation of a pump control module is illustrated in FIG. 12A, but the functionality of such a module can be generalized as follows. The system determines the light transmissivity of a separated blood component. The transmissivity is used as an input for calculating a weighted or adjusted flow rate, which is compared to the actual flow rate of the separated blood component. Whichever of the two flow rates is greater, the interface controller 12 will set the selected pump to operate at that flow rate.

Turning now to the specific implementation of the pump control module illustrated in FIG. 12A, the normalized transmission value of the separated plasma is compared to a threshold value, which is an empirically determined value resulting in the desired control protocol. As such, the threshold value may vary depending on the nature of the separation hardware and the particular separation procedure being executed. This process is represented in FIG. 12A by the diamond containing the words "Is Plasma Transmission>0.80?"

When the normalized transmission value is greater than the threshold value (0.80 in one embodiment, which is indicative of relatively clear plasma), the processing element 98 sets a multiplier equal to a first value. This process is represented in FIG. 12A by the box containing the words "Set multiplier to 0.60."

When the normalized transmission value is less than 0.80 (indicating relatively cloudy plasma), the processing element instead sets the multiplier to a second value. This process is represented in FIG. 12A by the box containing the words "Set multiplier to 0.75." As will be described in greater detail below, the multiplier serves to bias the system toward selecting one of a number of possible pump control responses.

The actual first and second multiplier values may vary from system to system and are typically determined by empirical testing to arrive at values which result in the proper pump control response being initiated. However, in the illustrated embodiment, a first value of 0.60 is a suitable multiplier when the normalized transmission value is greater than 0.80 and a second value of 0.75 is a suitable multiplier when the normalized transmission value is less than 0.80.

The processing element 98 then multiplies an ideal plasma flow rate $Q_{IDEAL}$ by the multiplier to arrive at a calculated value $Q_{ADJUSTED}$. The ideal plasma flow rate $Q_{IDEAL}$ is a calculated value based on the hematocrit of the blood (which may be determined prior to processing by known methods) and represents a theoretical plasma flow rate at which the interface is properly positioned within the system for optimal collection efficiency. In the illustrated system, the ideal plasma flow rate $Q_{IDEAL}$ is calculated using the following formula: $Q_{IDEAL}=Q_{WB}*(1-Hct_{WB}/Hct_{RBC})$, where $Q_{WB}$ is the flow rate of whole blood, $Hct_{WB}$ is the hematocrit of whole blood entering the system and $Hct_{RBC}$ is the hematocrit of the RBC layer 56 exiting the system. Other methods of calculating $Q_{IDEAL}$ may also be employed without departing from the scope of the present disclosure.

The calculated value $Q_{ADJUSTED}$ is compared to the actual plasma flow rate $Q_{ACTUAL}$ determined by the first optical sensor assembly 70 (which may be determined by any of a number of methods). The plasma flow rate is then set (typically by directly adjusting the operational rate of the plasma pump 100, if provided) to whichever of the two values is greater. This process is represented in FIG. 12A by the box containing the words "Is QP Ideal Mode=TRUE?"

It will be seen that the multiplier and, hence, $Q_{ADJUSTED}$ will be relatively small when the normalized transmission is greater (because the multiplier is 0.60 in the illustrated example) and will be relatively large when the normalized transmission is lower (because the multiplier is 0.75 in the illustrated example). Thus, it is more likely that the plasma flow rate will be set to $Q_{ACTUAL}$ when the plasma is relatively clear (i.e., probably normal and neither lipemic nor hemolytic) and more likely that the plasma flow rate will be set to $Q_{ADJUSTED}$ when the plasma is relatively cloudy (i.e., possibly lipemic or hemolytic). When the plasma is relatively clear, it may be preferred to set the plasma flow rate at $Q_{ACTUAL}$ for improved plasma contamination prevention. Similarly, when the plasma is more cloudy, it may be preferred to set the plasma flow rate at $Q_{ADJUSTED}$ for improved plasma removal efficiency.

Thus, by the foregoing control scheme, the transmissivity of the plasma may be used to select the plasma flow rate.

(2) Contamination Detection Module

The contamination detection module helps to select the most appropriate sensor assembly for monitoring separated plasma and preventing contamination thereof. A specific implementation of a contamination detection module is illustrated in FIG. 12B, but the functionality of such a module can be generalized as follows. The system determines the light transmissivity of a separated blood component. The transmissivity (or a value based at least in part upon the transmissivity) is used as a basis for selecting which of a number of contamination detectors to use and the contamination prevention steps to be carried out by the interface controller 12.

The contamination detection module may be employed separately from the pump control module. For example, if the pump control module is omitted, the transmissivity of the separated blood component may be determined and normalized (e.g., as described above in reference to operation of the pump control module and as illustrated in FIG. 12A by the boxes containing the words "Calculate red transmission" and "Normalize Plasma Transmission using Saline Transmission"). If the normalized transmission value is greater than a particular level, the separated blood component is considered "relatively clear" and certain steps are performed (as described in greater detail below). If the normalized transmission value is less than the selected level, the separated blood component is considered "relatively cloudy" and different steps are performed (as described in greater detail below).

However, while the contamination detection module may be employed independently, it may be advantageous for the contamination detection module to be executed following the pump control module (as illustrated by the arrows extending from FIG. 12A to FIG. 12B) for improved plasma collection efficiency. When both modules are employed, the normalized transmission value may be used as an input to the contamination detection module, similar to when the pump control module is omitted. Alternatively, the output of the pump control module (which is based in part on the transmissivity of the separated blood component) may be employed to designate whether the separated blood component is "relatively clear" or "relatively cloudy." In one preferred embodiment (employing the pump control module of FIG. 12A), if the plasma flow rate is set to $Q_{ACTUAL}$ by the pump control module (as described above), then it is an indication that the plasma is "relatively clear" (i.e., neither lipemic nor hemolytic and with a sufficiently high normalized transmission value). On the other hand, if the plasma flow rate is set to $Q_{ADJUSTED}$ by the pump control module (as described above), then it is an indication that the plasma is "relatively cloudy" (i.e., it may be either lipemic or hemolytic).

(a) Relatively Clear Plasma

When it is determined that the plasma is "relatively clear" (per the foregoing criteria or any other suitable criteria), it is safe for the interface controller 12 to select the first optical sensor assembly 70 for contamination detection duty (i.e., monitoring the separated plasma for the presence of cellular components). This process is represented in FIG. 12B by the rightmost box containing the words "Enable spill detection by interface detector." When the first optical sensor assembly 70 has been selected for further process monitoring, the second optical sensor assembly 72 is disabled of its contamination detection functionality. This process is represented in FIG. 12B by the rightmost box containing the words "Disable spill detection by top panel optical sensor."

When it has been selected for further process monitoring, the first optical sensor assembly 70 operates to determine whether the separated plasma has been contaminated by a spillover (i.e., by cellular blood components spilling into the plasma outlet line). This process is represented in FIG. 12B by the rightmost diamond containing the words "Spillover detected by interface detector?" Many methods of optically detecting plasma contamination are in practice today and known to those of ordinary skill in the art and any of these methods (or methods yet to be practiced) may be employed without departing from the scope of the present disclosure.

If the first optical sensor assembly 70 finds there to be no contamination of the plasma, then the control system returns to its initial step and the process repeats itself. This is represented in FIGS. 12A and 12B by the "NO" arrow leading from the rightmost diamond containing the words "Spillover detected by interface detector?" (FIG. 12B) to the box containing the words "Calculate red transmission" (FIG. 12A).

If the first optical sensor assembly 70 detects contamination of the plasma, then the control system takes steps to counteract the contamination. This is represented in FIG. 12B by the rightmost box containing the words "Perform spillover recovery." Many methods of counteracting plasma contamination are in practice today and known to those of ordinary skill in the art and any of these methods (or methods yet to be practiced) may be employed without departing from the scope of the present disclosure. For example, the system may respond to a spill by reversing the flow in the outlet line 94 until the spill clears. In another embodiment, the operation of the plasma pump 100 is slowed and the outflowing plasma is temporarily diverted from a collection container to the donor or patient until the spill clears, at which time collection of the plasma may resume. When the anti-contamination steps have been carried out, the control system returns to its initial step and the process repeats itself. This is represented in FIGS. 12A and 12B by the arrow leading from the rightmost box containing the words "Perform spillover recovery" (FIG. 12B) to the box containing the words "Calculate red transmission" (FIG. 12A).

(b) Relatively Cloudy Plasma

On the other hand, if it is determined that the plasma is "relatively cloudy" (per the foregoing criteria or any other suitable criteria), then another calculation is made prior to selecting the appropriate sensor assembly for further process monitoring. This process is represented in FIG. 12B by the diamond containing the words "Is Plasma Transmission<Lipid_Level?"

In particular, the normalized plasma transmission value is compared to a "Lipid_" value, which is indicative of the presence of excess lipids or hemoglobin in the plasma layer 58. This value may vary from system to system and is typically determined by empirical testing to arrive at a value which results in the proper optical sensor assembly being selected for further process monitoring. However, in one embodiment, a "Lipid_Level" value of 0.7 is selected to compare against the normalized plasma transmission value.

(i) Normalized Plasma Transmission Value Greater than Lipid_Level Value

If the normalized plasma transmission value is greater than 0.7 (or whatever the "Lipid_Level" value may be), then it is an indication that the plasma layer 58, while being relatively cloudy, is only slightly lipemic or hemolytic, in which case it is acceptable for the interface controller 12 to select the first optical sensor assembly 70 to serve as the interface detector. This process is represented in FIG. 12B by the leftmost box containing the words "Enable spill detection by interface detector" (i.e., at the end of the "NO" arrow leading from the diamond containing the words "Is Plasma Transmission<Lipid_Level?"). When the first optical sensor assembly 70 has been selected for further process monitoring, the second optical sensor assembly 72 is disabled of its contamination detection functionality. This process is represented in FIG. 12B by the leftmost box containing the words "Disable spill detection by top panel optical sensor."

When it has been selected for further process monitoring, the first optical sensor assembly 70 operates to determine whether the separated plasma has been contaminated by cellular blood components spilling into the plasma. This process is represented in FIG. 12B by the leftmost diamond containing the words "Spillover detected by interface detector?" Many methods of optically detecting plasma contamination are in practice today and known to those of ordinary skill in the art and any of these methods (or methods yet to be practiced) may be employed without departing from the scope of the present disclosure.

If the first optical sensor assembly 70 finds there to be no contamination of the plasma, then the control system returns to its initial step and the process repeats itself. This is represented in FIGS. 12A and 12B by the "NO" arrow leading from the leftmost diamond containing the words "Spillover detected by interface detector?" (FIG. 12B) to the box containing the words "Calculate red transmission" (FIG. 12A).

If the first optical sensor assembly 70 detects contamination of the plasma, then the control system takes steps to counteract the contamination. In the illustrated embodiment, this is represented in FIG. 12B by the rightmost box containing the words "Decrease plasma rate by 10%" and the center box containing the words "Perform spillover recovery."

If the control system is performing the "relatively cloudy plasma" routine and contamination of the plasma layer 58 is detected, it is an indication that the interface 60 may be closer to the low-G wall 64 than it should be. Thus, it may be desirable to decrease the plasma rate by some factor to increase the height of the plasma layer 58 on the ramp 66, which has the effect of moving the interface 60 away from the low-G wall 64. In the illustrated embodiment, the plasma rate is decreased by 10%, but it may also be decreased by some other factor without departing from the scope of the present disclosure.

As for the spillover recovery steps performed by the system, many methods of counteracting plasma contamination (e.g., by attempting to draw plasma from the outlet line 94 back into the first stage 24) are in practice today and known to those of ordinary skill in the art and any of these methods (or methods yet to be practiced) may be employed without departing from the scope of the present disclosure.

When the anti-contamination steps have been carried out, the control system returns to its initial step and the process repeats itself. This is represented in FIGS. 12A and 12B by the arrow leading from the center box containing the words "Perform spillover recovery" (FIG. 12B) to the box containing the words "Calculate red transmission" (FIG. 12A).

(ii) Normalized Plasma Transmission Value Less than Lipid_Level Value

If the normalized value is less than 0.7 (or whatever the "Lipid_Level" value may be), then it is an indication that the cloudiness of the plasma layer 58 is due to the plasma being lipemic or hemolytic and that the first optical sensor assembly 70 is not suitable for properly monitoring the location of the interface 60 and preventing plasma contamination. In this case, the second optical sensor assembly 72 is selected as the interface detector. This process is represented in FIG. 12B by the box containing the words "Enable spill detection by top panel optical sensor" (i.e., at the end of the "YES" arrow leading from the diamond containing the words "Is Plasma Transmission<Lipid_Level?"). When the second optical sensor assembly 72 has been selected for further process monitoring, the first optical sensor assembly 70 is disabled of its contamination detection functionality. This process is represented in FIG. 12B by the box containing the words "Disable spill detection by interface detector."

In general, it may be preferred to use the first optical sensor assembly 70 instead of the second optical sensor assembly 72 for contamination detection (e.g., because the first optical sensor assembly 70 is located further upstream in the system and may be better suited to avoiding plasma contamination). However, as described above, if the plasma is lipemic or hemolytic, conventional interface control means are unsuitable and the automated control system of the present invention is preferred to known systems, which must resort to manual inspection and intervention when processing lipemic or hemolytic plasma.

When the second optical sensor assembly 72 has been chosen for further process monitoring, it operates to determine whether the separated plasma has been contaminated by cellular blood components spilling into the plasma. This process is represented in FIG. 12B by the diamond containing the words "Spillover detected by top panel optical sensor?" The second optical sensor assembly 72 compares the transmissivity of the plasma layer 58 to a minimum transmission value which is indicative of contamination of the plasma layer 58. When the plasma layer 58 is contaminated, the second optical sensor assembly 72 will be "blinded" by cellular components, thereby drastically reducing the normalized plasma transmission value. For example, in one embodiment, the second optical sensor assembly 72 will only register contamination upon a normalized transmission value less than 0.1, which is much lower than the normalized transmission value of even highly lipemic or hemolytic plasma.

If the normalized transmission value is greater than or equal to 0.1 (i.e., that the plasma is lipemic or hemolytic, but not contaminated by cellular blood components), then the control system returns to its initial step and the process repeats itself. This is represented in FIGS. 12A and 12B by the "NO" arrow leading from the leftmost diamond containing the words "Spillover detected by top panel optical sensor?" (FIG. 12B) to the box containing the words "Calculate red transmission" (FIG. 12A).

On the other hand, if the normalized transmission value is less than 0.1, it is an indication that the plasma layer 58 has been contaminated. Various steps may be taken to respond to contamination but, in the illustrated embodiment, the interface command element 88 responds by decreasing the plasma flow rate (e.g., by 10% in the illustrated embodiment) and then initializing a "perform spillover recovery" step. These steps are illustrated in FIG. 12B by the leftmost box containing the words "Decrease plasma rate by 10%" and the leftmost box containing the words "Perform spillover recovery." The purpose of decreasing the plasma rate is to move the interface 60 away from the low-G wall 64, thereby decreasing the likelihood of future contamination.

The anti-contamination steps carried out by the interface command element 88 may be either the same as those performed in the event of plasma contamination when the normalized transmission value is greater than the "Lipid_Level" value or different. When the anti-contamination steps have been carried out, the control system returns to its initial step and the process repeats itself. This is represented in FIGS. 12A and 12B by the arrow leading from the leftmost box containing the words "Perform spillover recovery" (FIG. 12B) to the box containing the words "Calculate red transmission" (FIG. 12A).

(3) Subsequent Iterations

The step of checking the saline transmissivity (i.e., the step represented in FIG. 12A by the box containing the words "Obtain Saline Transmission at start of Initial Processing") may be avoided or eliminated once a subsequent iteration of the control process begins, as the same saline transmissivity value which is initially determined may be used for the entire procedure.

The control process of FIGS. 12A and 12B may be repeated periodically, for example, once every second. If the process repeatedly finds that the separated plasma is sufficiently cloudy or turbid (e.g., with a normalized plasma transmission value less than 0.80), but not contaminated (e.g., registering a normalized plasma transmission value greater than or equal to 0.1), then the system may trigger an alarm or indicator which signifies that the plasma is lipemic or hemolytic. In one embodiment, this alarm or indicator is only triggered once and only if the normalized transmission value falls within the aforementioned range for five consecutive seconds.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of separating blood into one blood component and other blood components, comprising:
    separating blood in a blood separation chamber into at least one blood component and a different other blood component;
    monitoring the interior of the blood separation chamber with a first optical sensor assembly;
    removing at least a portion of the at least one blood component from the blood separation chamber;
    monitoring, while blood is being separated, the at least one blood component removed from the blood separation chamber with a second optical sensor assembly; and
    selecting, while blood is being separated, only one of the first optical sensor assembly or the secondary optical sensor assembly for detecting the presence of said different other blood component in the at least one blood component, wherein the first optical sensor assembly is selected under a first condition in which the at least one blood component has a first light transmissivity and wherein the second optical sensor assembly is selected under a second condition in which the at least one blood component has a second light transmissivity.

2. The method of claim 1, wherein said monitoring the at least one blood component removed from the blood separation chamber includes determining whether the at least one blood component is lipemic or hemolytic.

3. The method of claim 2, wherein said selecting the first optical sensor assembly or the second optical assembly for detecting the presence of said different other blood component in the at least one blood component includes selecting the second optical assembly if the at least one blood component is lipemic or hemolytic and selecting the first optical sensor assembly if the at least one blood component is neither lipemic nor hemolytic.

4. The method of claim 1, wherein said at least one blood component comprises substantially cell-free plasma.

5. The method of claim 1, wherein said removing at least a portion of the at least one blood component from the blood separation chamber includes removing at least a portion of the at least one blood component from the blood separation chamber at a rate, and further comprising a step of controlling said rate based at least in part on the light transmissivity of the at least one blood component.

* * * * *